US008565846B2

(12) United States Patent
Ono et al.

(10) Patent No.: US 8,565,846 B2
(45) Date of Patent: Oct. 22, 2013

(54) BLOOD OXYGEN SATURATION MEASURING APPARATUS

(75) Inventors: Yoshinobu Ono, Tokyo (JP); Takeshi Kojima, Tokyo (JP); Jun Motogi, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 502 days.

(21) Appl. No.: 12/710,339

(22) Filed: Feb. 22, 2010

(65) Prior Publication Data

US 2011/0046462 A1    Feb. 24, 2011

(30) Foreign Application Priority Data

Feb. 23, 2009   (JP) ................................. 2009-039253

(51) Int. Cl.
*A61B 5/00*  (2006.01)

(52) U.S. Cl.
USPC .......................................................... 600/323

(58) Field of Classification Search
USPC ........................................ 600/324, 323, 331
See application file for complete search history.

(56) References Cited

U.S. PATENT DOCUMENTS

| 4,765,340 | A | * | 8/1988 | Sakai et al. ................... 600/324 |
| 5,253,646 | A | | 10/1993 | Delpy et al. |
| 5,385,144 | A | * | 1/1995 | Yamanishi et al. ........... 600/330 |
| 6,018,673 | A | | 1/2000 | Chin et al. |
| 2004/0215095 | A1 | | 10/2004 | Lee et al. |
| 2005/0222502 | A1 | * | 10/2005 | Cooper ......................... 600/323 |
| 2005/0256386 | A1 | | 11/2005 | Chan et al. |
| 2006/0009688 | A1 | | 1/2006 | Lamego et al. |
| 2006/0105319 | A1 | | 5/2006 | Rees et al. |
| 2006/0241506 | A1 | | 10/2006 | Melker et al. |
| 2007/0049811 | A1 | | 3/2007 | Kobayashi et al. |
| 2008/0262327 | A1 | | 10/2008 | Kato |

FOREIGN PATENT DOCUMENTS

| JP | 61-228831 A | 10/1986 |
| JP | 63-5729 A | 1/1988 |
| JP | 5-245129 A | 9/1993 |
| JP | 10-507118 A | 7/1998 |
| JP | 10-216114 A | 8/1998 |
| JP | 2001-501847 A | 2/2001 |
| JP | 2004-8572 A | 1/2004 |
| JP | 2004-321807 A | 11/2004 |

(Continued)

OTHER PUBLICATIONS

Japanese Office Action for the related Japanese Patent Application No. 2009-039253 dated Oct. 5, 2012.

*Primary Examiner* — Clayton E Laballe
*Assistant Examiner* — Noam Reisner
(74) *Attorney, Agent, or Firm* — Kenealy Vaidya LLP

(57) ABSTRACT

A blood oxygen saturation measuring apparatus includes: a light emitter adapted to emit, to living tissue of a subject, at least two light beams which have different wavelengths from each other; a light receiver adapted to receive the light beams which are transmitted through or reflected from the living tissue, the light receiver which converts the received light beams to electric signals corresponding to receiving intensities of the light beams, respectively; an extractor which extracts frequency components corresponding to changes of the receiving intensities according to a variation of a blood volume of a vein in the living tissue due to respiration of the subject, from the electric signals, respectively; an attenuation ratio calculator which calculates a first attenuation ratio based on amplitudes of the extracted frequency components; and an oxygen saturation calculator which calculates a first blood oxygen saturation in the vein based on the first attenuation ratio.

2 Claims, 9 Drawing Sheets

(56) References Cited

FOREIGN PATENT DOCUMENTS

| JP | 2005-52385 A | 3/2005 |
| JP | 2005-528134 A | 9/2005 |
| JP | 2005-534018 A | 11/2005 |
| JP | 2007-83021 A | 4/2007 |
| JP | 2008-505691 A | 2/2008 |
| JP | 2008-538936 A | 11/2008 |
| WO | 2006/009178 A1 | 1/2006 |
| WO | 2008/071643 A1 | 6/2008 |
| WO | 2008/134813 A1 | 11/2008 |

* cited by examiner

BLOOD OXYGEN SATURATION MEASURING APPARATUS

BACKGROUND OF THE INVENTION

The present invention relates to a blood oxygen saturation measuring apparatus which measures an oxygen saturation of a subject to be measured.

In order to detect a symptom of the sleep apnea syndrome, various related-art apparatuses and methods have been proposed. Among them, a related-art oxygen saturation measuring apparatus is known which obtains the oxygen saturation in arterial blood of the subject to estimate the respiratory motion of the subject, i.e., the variation in intrathoracic pressure (for example, see JP-A-10-216114).

As an oxygen saturation measuring apparatus, a pulse oximeter is used in which light beams of plural wavelengths that are different in light absorbency to the target substance such as oxygenated hemoglobin are transmitted through or reflected from living tissue, the intensity of reflected or transmitted light is continuously measured, and the oxygen saturation (SpO2) in arterial blood is obtained from a pulse wave data signal obtained in the measurement.

In the related-art oxygen saturation measuring apparatus disclosed in JP-A-10-216114, the respiratory status of the subject is monitored by measuring the oxygen saturation in arterial blood, and hence a time lag occurs between an obstructive apnea condition of the subject and a significant reduction of the oxygen saturation in arterial blood. In the case where the subject enters a central apnea condition during sleep, the reduction of the oxygen saturation in arterial blood is very gentle. Consequently, there is a problem in that, based on only the measured value of the oxygen saturation, it is difficult to determine whether the respiratory motion is normally performed or a central apnea condition occurs.

Furthermore, a related-art method has been proposed in which a respiration detector including a thermistor and a cannula sensor is attached between the nose and the upper lip to measure changes of the temperature and the pressure due to nasal air flow, and band-like strain gauges are wound around the chest and the abdomen to measure the phase difference and degrees of the motions of the chest and the abdomen, thereby detecting a central apnea condition. In the related-art method, however, the number of electrodes or the like to be attached is large. Therefore, for example, it is difficult to stably perform the respiratory management of a neonatal infant, because of error causes such as body motion.

SUMMARY

It is therefore an object of the invention to provide an oxygen saturation measuring apparatus which can detect at an earlier timing that a subject enters an obstructive apnea condition.

In order to achieve the object, according to the invention, there is provided a blood oxygen saturation measuring apparatus comprising:

a light emitter adapted to emit, to living tissue of a subject, at least two light beams which have different wavelengths from each other;

a light receiver adapted to receive the light beams which are transmitted through or reflected from the living tissue, the light receiver which converts the received light beams to electric signals corresponding to receiving intensities of the light beams, respectively;

an extractor which extracts frequency components corresponding to changes of the receiving intensities according to a variation of a blood volume of a vein in the living tissue due to respiration of the subject, from the electric signals, respectively;

an attenuation ratio calculator which calculates a first attenuation ratio based on amplitudes of the extracted frequency components; and an oxygen saturation calculator which calculates a first blood oxygen saturation in the vein based on the first attenuation ratio.

The blood oxygen saturation measuring apparatus may further include: a determiner which determines that the subject is in an obstructive apnea condition, when the first blood oxygen saturation in the vein shows a decreasing trend for a predetermined time period or longer.

The determiner may determine that the subject is in a central apnea condition, when the amplitudes of the frequency components are smaller than a predetermined value for a predetermined time period or longer.

The extractor may extract pulsation components corresponding to changes of the receiving intensities according to pulsation of an artery in the living tissue, from the electric signals, respectively. The attenuation ratio calculator may calculate a second attenuation ratio based on amplitudes of the pulsation components. The oxygen saturation calculator may calculate a second blood oxygen saturation in the artery based on the second attenuation ratio. The determiner may determine that the subject is in a central apnea condition, when the amplitudes of the frequency components are smaller than a predetermined value for a predetermined time period or longer and the second blood oxygen saturation in the artery does not show a decreasing trend.

The blood oxygen saturation measuring apparatus may further include: a body motion detector which detects a change of body motion of the subject. The oxygen saturation calculator may correct the calculated first blood oxygen saturation based on the change of the body motion.

DETAILED DESCRIPTION OF EMBODIMENTS

Hereinafter, the invention will be described through an embodiment of the invention. The invention set forth in claims is not restricted by the following embodiment. All of the combinations of the features described in the embodiment are not always essential to the solving means of the invention.

Figure 1:
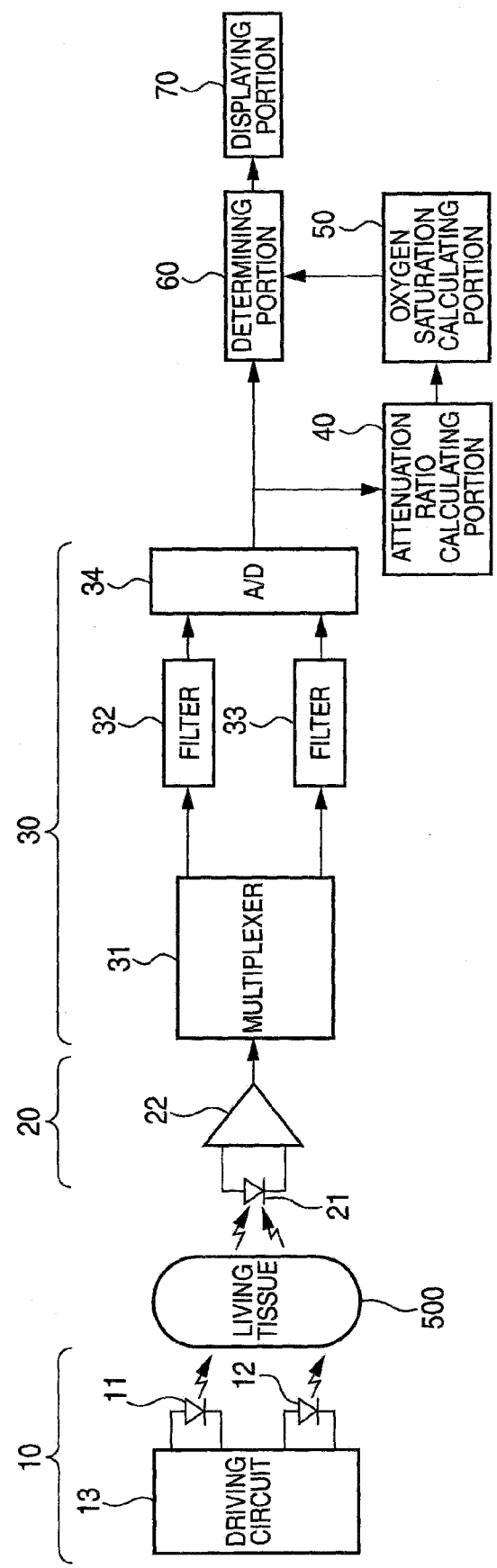
FIG. 1 is a functional block diagram of a blood oxygen saturation measuring apparatus of an embodiment of the invention.

FIG. 1 is a functional block diagram of a blood oxygen saturation measuring apparatus 100 of the embodiment of the invention. As shown in FIG. 1, the blood oxygen saturation measuring apparatus 100 is an apparatus for measuring the oxygen saturation in the vein of the subject, and includes a light emitter 10, a light receiver 20, an extracting portion 30, an attenuation ratio calculating portion 40, an oxygen saturation calculating portion 50, a determining portion 60, and a displaying portion 70.

The light emitter 10 has light emitting elements 11, 12 and a driving circuit 13. The light emitting elements 11, 12 are driven by the driving circuit 13 so as to alternately emit two light beams of different wavelengths. In the example, the light emitting element 11 is a light emitting diode which emits an infrared light beam (IR) of a wavelength of about 940 nm, and the light emitting element 12 is a light emitting diode which emits a red light beam (R) of a wavelength of about 660 nm.

The wavelengths of the light beams emitted from the light emitting elements 11, 12 are not restricted to the above-described ones. For example, the wavelength of the light beam emitted from the light emitting element 11 is preferably set to a value which is within a region where the difference between the absorptivity of oxygenated hemoglobin in the blood and that of deoxygenated hemoglobin is larger than a predetermined value, specifically, a wavelength band shorter than 800 nm, and which is as large as possible. For example, the wavelength of the light beam emitted from the light emitting element 12 is preferably set to a value which is within a region where the difference between the absorptivity of oxygenated hemoglobin in the blood and that of deoxygenated hemoglobin is smaller than the predetermined value, specifically, a wavelength band longer than 800 nm, and which is as small as possible.

The light receiver 20 has a light receiving element 21 and an amplifier 22. When the light beams of the two different wavelengths emitted from the light emitter 10 alternately impinge on the living tissue 500 of the subject, the light receiving element 21 receives the light beams of the respective wavelengths which are transmitted through or reflected from the living tissue 500, and converts the light beams to an electric signal corresponding to the receiving intensities of the light beams. The amplifier 22 amplifies the electric signal supplied from the light receiving element 21, by a predetermined factor. In the example, the light receiving element 21 is a photodiode, and the living tissue 500 may be, for example, the tip of a finger or an ear lobe of the subject.

The extracting portion 30 has a multiplexer 31, a filter 32, a filter 33, and an A/D converter 34. The multiplexer 31 separates the electric signal which is amplified in the amplifier 22, into electric signals respectively corresponding to the light wavelengths (R and IR). The electric signals which are obtained by the separation in the multiplexer 31 are input into the filters 32, 33, respectively.

Figure 2:
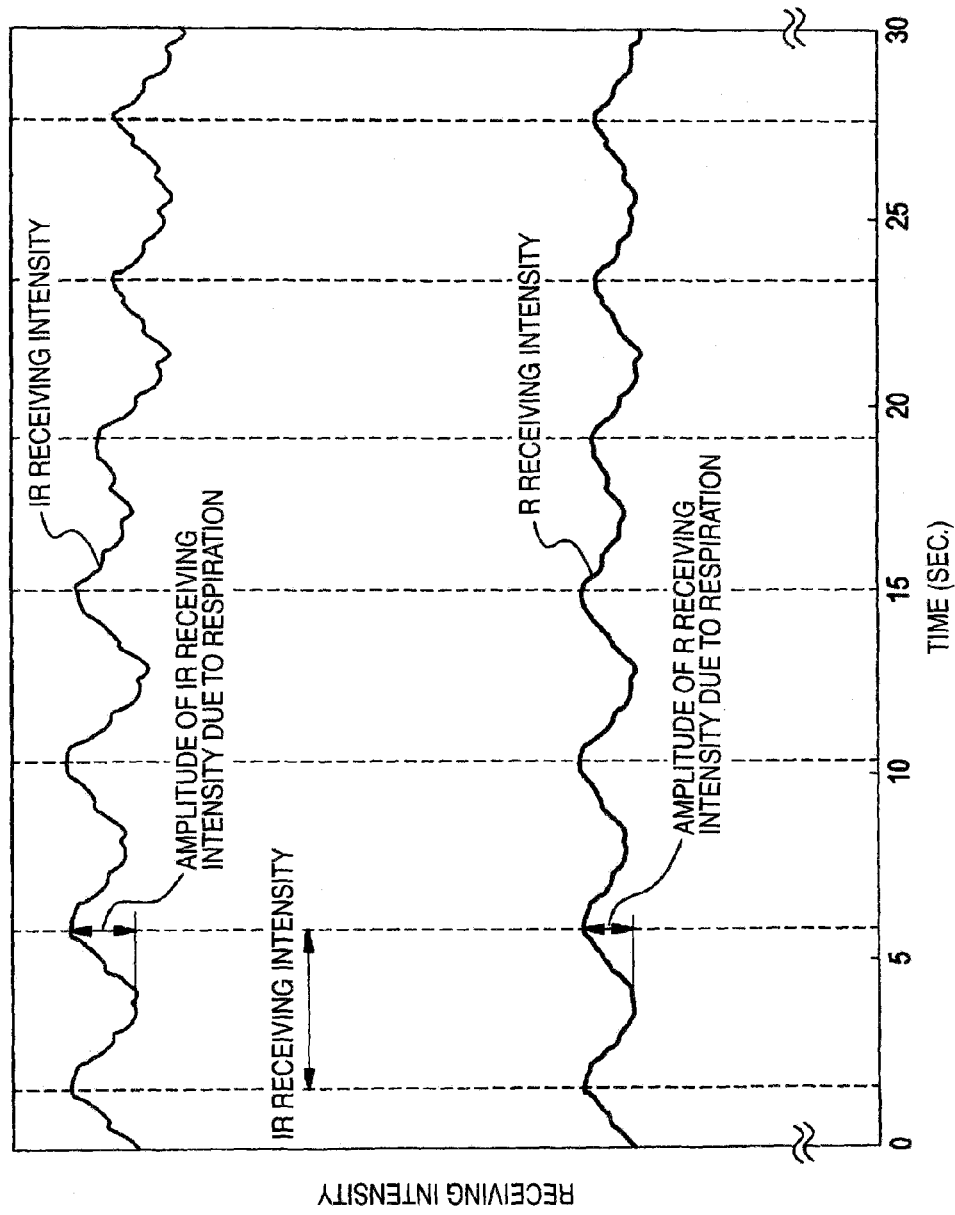
FIG. 2 is a graph showing examples of signal waveforms which are input into filters, respectively.

FIG. 2 is a graph showing examples of signal waveforms which are input into the filters 32, 33, respectively. As shown in FIG. 2, the electric signals containing components which vary in accordance with the respiratory rate, and respectively corresponding to R and IR.

The filters 32, 33 extracts specific frequency components in the input electric signals, and filter out components other than the frequency components. The A/D converter 34 digitizes the electric signals which are filtered in the filters 32, 33, respectively. The frequency components which are extracted in the filters 32, 33 correspond to the variation period of the blood volume of the vein in the living tissue 500, in variation components of the input electric signals.

The variation of the blood volume of the vein is caused by the phenomenon in which the intrathoracic pressure is varied in accordance with the respiration of the subject to press the heart, and the amount of the venous blood refluxing to the heart is periodically varied. Therefore, the frequency components which are extracted in the filters 32, 33 substantially coincide with components which are in the light beams of the two wavelengths impinging from the light emitter 10 on the living tissue 500, and which are periodically varied in receiving intensity in the light receiver 20 in accordance with the respiratory rate of the subject.

In the case where the respiratory rate of the subject is unknown, a frequency analyzing portion which can perform a fast Fourie-transformation on an incoming electric signal may be disposed in front stages of each of the filters 32, 33, so that the frequencies of the electric signals respectively corresponding to R and IR are analyzed and the frequency components corresponding to the respiratory rate of the subject are specified. In this case, preferably, the filters 32, 33 are variable bandpass filters in which the frequency components to be extracted can be changed following the variations in the respiratory rate measured by the respective frequency analyzing portions in the front stage.

The attenuation ratio calculating portion 40 calculates the attenuation ratio on the basis of the amplitudes of the frequency components which are extracted in the extracting portion 30 with respect to the electric signals respectively corresponding to the light beams of the two wavelengths. In the attenuation ratio calculating portion 40, specifically, each of the electric signals corresponding to R and IR is separated into AC and DC components, and the ratio of AC/DC is calculated for each of the signals. Then, the ratio of $AC_R/DC_R$ which is calculated with respect to R is divided by that of $AC_{IR}/DC_{IR}$ which is calculated with respect to IR to calculate their ratio (attenuation ratio) $R_{(R/IR)}$ [$(AC_R/DC_R)/(AC_{IR}/DC_{IR})$].

The oxygen saturation calculating portion 50 calculates the blood oxygen saturation in the vein in the living tissue 500 on the basis of the attenuation ratio $R_{(R/IR)}$ which is calculated in the attenuation ratio calculating portion 40. As the method of calculating the blood oxygen saturation, any one of various related-art methods may be used.

The determining portion 60 monitors the blood oxygen saturation which is calculated in the oxygen saturation calculating portion 50, and displays the current value, temporal change, and the like of the blood oxygen saturation, on the displaying portion 70. When a decreasing trend of the blood oxygen saturation continues for a predetermined time period or longer, for example, the determining portion 60 determines that the subject is in an obstructive apnea condition, and displays the determination result on the displaying portion 70.

Figure 3:
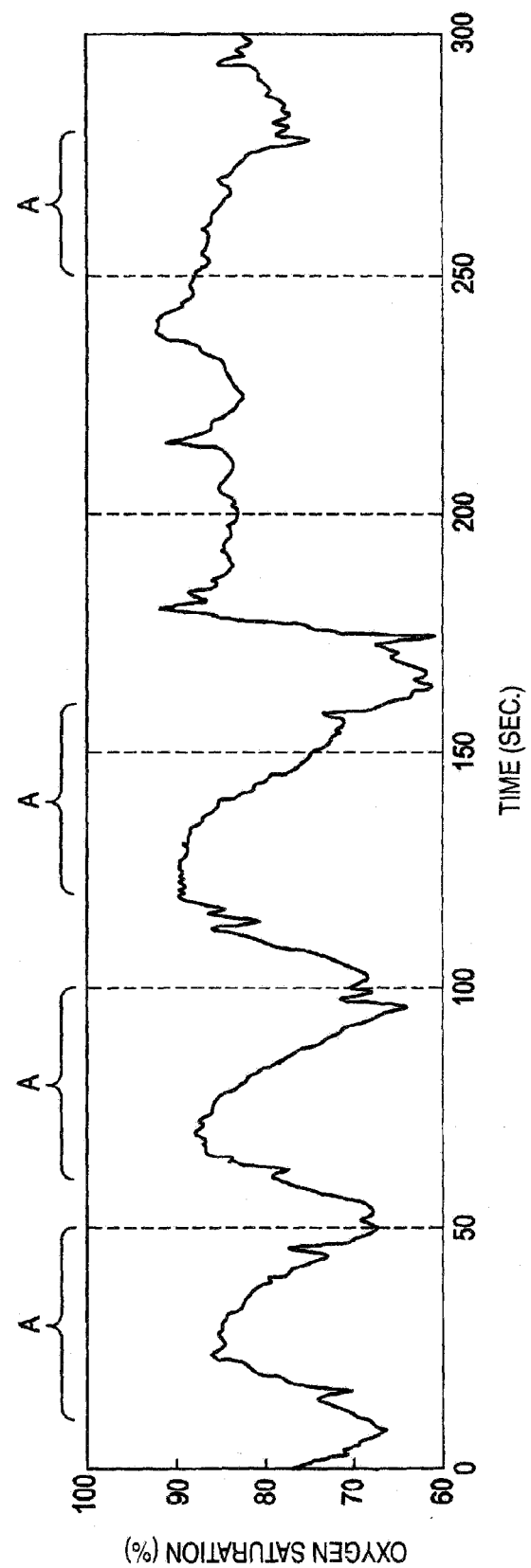
FIG. 3 is a view showing an example of a temporal change of the blood oxygen saturation in the vein.

FIG. 3 shows an example of the temporal change of the blood oxygen saturation in the vein. In the example, the subject is suspected of being in an obstructive apnea condition, for example, in time zones which are indicated by "A" in the upper portion of the graph of FIG. 3. When the blood oxygen saturation shows a decreasing trend in the time zones, the determining portion 60 determines that the subject is in an obstructive apnea condition, in accordance with the setting of the predetermined time period.

Furthermore, the determining portion 60 monitors the amplitudes of the frequency components which are extracted from the electric signal respectively corresponding to R and IR in the extracting portion 30. The determining portion 60 may display temporal variations of the amplitudes on the displaying portion 70. When the amplitudes are lower than a predetermined value for a predetermined time period or longer, for example, the determining portion 60 determines that the subject is in a central apnea condition such as a hypoventilation respiratory failure, and displays the determination result on the displaying portion 70.

Figure 4:
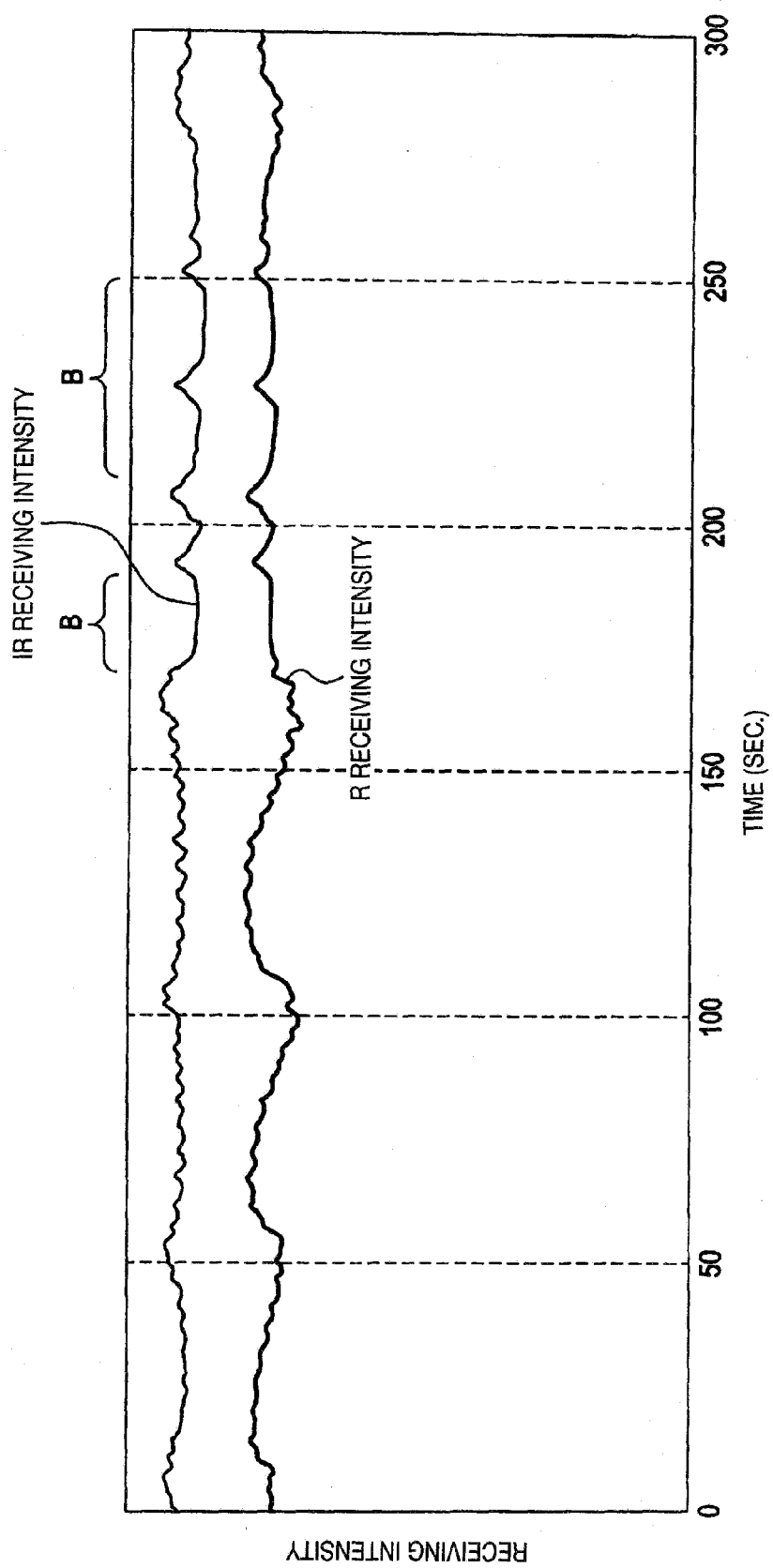
FIG. 4 is a view showing the waveforms of electric signals corresponding to R and IR used in the calculation of the blood oxygen saturation in the vein shown in FIG. 3.

FIG. 4 shows the waveforms of the electric signals corresponding to R and IR used in the calculation of the blood oxygen saturation in the vein shown in FIG. 3. In the example, the subject is suspected of being in a central apnea condition, for example, in time zones which are indicated by "B" in the upper portion of the graph of FIG. 4. When the amplitudes satisfy the above-mentioned conditions in the time zones, the determining portion 60 determines that the subject is in an obstructive apnea condition.

The determining portion 60 may output the determination result to an external storage device or a communication line (both are not shown), or notify the subject of the like of the result by means of an alarm. The predetermined time periods, and the like may be set in accordance with a symptom or the like which is assumed in the subject.

As described above, in the blood oxygen saturation measuring apparatus 100 of the embodiment, variation components of the blood volume of the vein are extracted from the electric signal corresponding to the light beams of the two wavelengths received by the light receiver 20, and the blood oxygen saturation is calculated. As compared with a blood oxygen saturation which is calculated by using the pulse wave component of the artery, in the calculated blood oxygen saturation, when the subject enters an obstructive apnea condition, a decreasing trend of the blood oxygen saturation appears at an earlier timing. According to the blood oxygen saturation measuring apparatus 100 of the embodiment, therefore, it is possible to detect at an earlier timing that the subject enters an obstructive apnea condition.

In the blood oxygen saturation measuring apparatus 100 of the embodiment, furthermore, the variation component of the blood volume of the vein is extracted, and the amplitude of the component is monitored. Therefore, it is possible to detect a central apnea condition during sleep which is hardly detected based on only the blood oxygen saturation that is calculated by using the pulse wave component of the artery. Simply when the light emitter 10 and the light receiver 20 are placed on the tip of a finger, an ear lobe, or the like of the subject, moreover, the blood oxygen saturation measuring apparatus 100 can perform the measurement. Therefore, the burden on the subject can be reduced and the measurement is insusceptible to body motion and the like.

Figure 5:
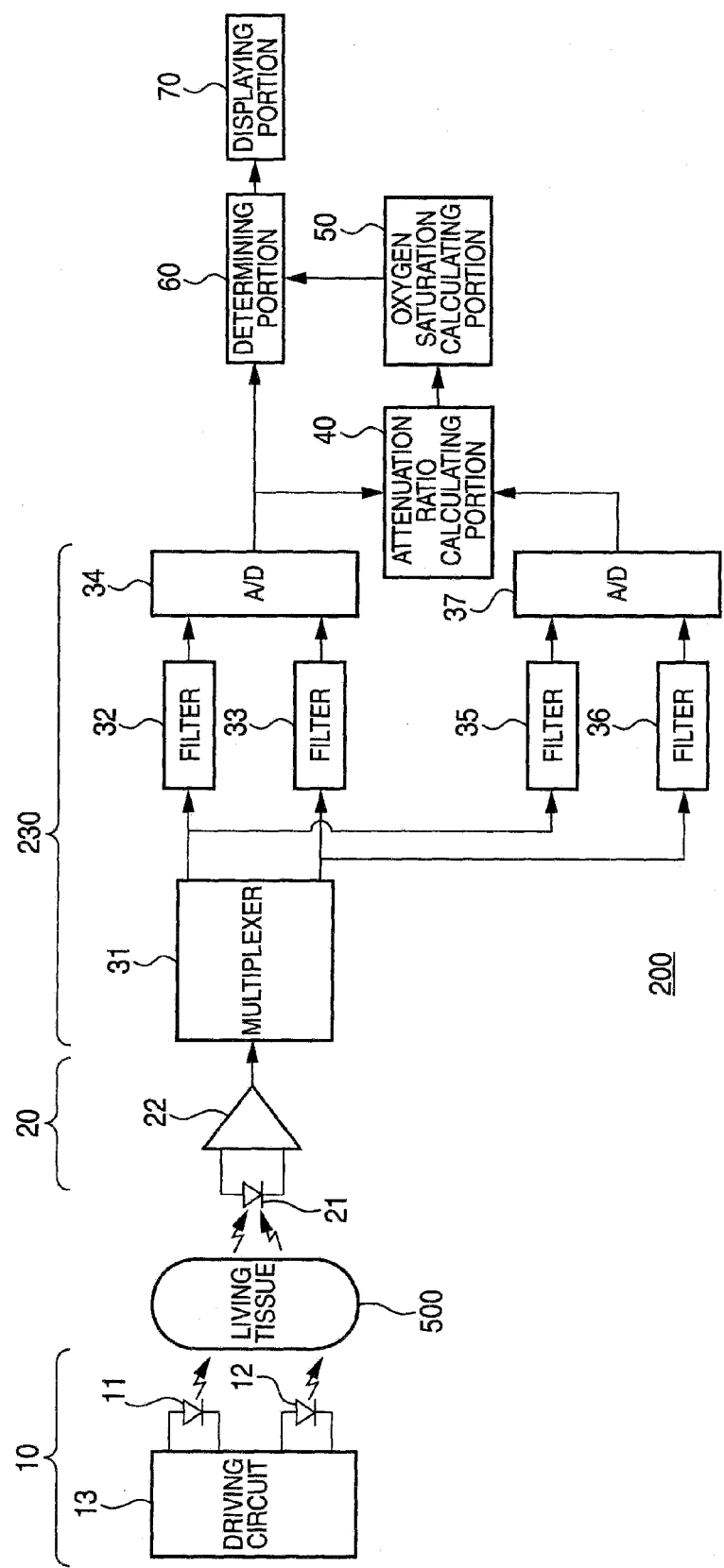
FIG. 5 is a functional block diagram of a blood oxygen saturation measuring apparatus of another example of the embodiment of the invention.

FIG. 5 is a functional block diagram of a blood oxygen saturation measuring apparatus 200 of another example of the embodiment of the invention. In the example, the configurations which are identical with those of the blood oxygen saturation measuring apparatus 100 which has been described with reference to FIG. 1 are denoted by the same reference numerals, and their description is omitted.

As shown in FIG. 5, the blood oxygen saturation measuring apparatus 200 includes an extracting portion 230 in place of the extracting portion 30 in the blood oxygen saturation measuring apparatus 100. The extracting portion 230 further has a filter 35, a filter 36, and an A/D converter 37 in addition to the configuration of the extracting portion 30.

The electric signals which are obtained by the separation in the multiplexer 31 are input into the filters 35, 36, respectively. In the example, the electric signal which is identical with that input into the filter 32 is input into the filter 35, and the electric signal which is identical with that input into the filter 33 is input into the filter 36.

The filters 35, 36 extract specific frequency components in the input electric signals, and filter out components other than the frequency components. The A/D converter 37 digitizes the electric signals which are filtered in the filters 35, 36. The frequency components which are extracted in the filters 35, 36 correspond to the pulsation rate of the artery in the living tissue 500, in variation components of the input electric signals.

The attenuation ratio calculating portion 40 calculates the attenuation ratio $R_{(R/IR)}$ on the basis of the electric signals which are extracted in the filters 32, 33 and digitized in the A/D converter 34, and further an attenuation ratio $R_{(R/IR)}'$ on the basis of the electric signals which are extracted in the filters 35, 36 and digitized in the A/D converter 37.

The oxygen saturation calculating portion 50 calculates the blood oxygen saturation in the vein on the basis of the attenuation ratio $R_{(R/IR)}$, and further calculates the blood oxygen saturation in the artery on the basis of the attenuation ratio $R_{(R/IR)}'$. As the method of calculating the blood oxygen saturation in the artery, any one of various related-art methods may be used.

The determining portion 60 monitors the blood oxygen saturation in the vein and that in the artery which are calculated in the oxygen saturation calculating portion 50, and displays the current values, temporal changes, and the like of the blood oxygen saturations, on the displaying portion 70. The determining portion 60 performs the determination on an obstructive apnea condition similarly with the determining portion 60 of the blood oxygen saturation measuring apparatus 100, and further determines that the subject is in a central apnea condition, under conditions that the amplitudes of the frequency components corresponding to the respiratory rate of the subject are lower than a predetermined value for a predetermined time period or longer, and the blood oxygen saturation in the artery does not show a decreasing trend.

Figure 6:
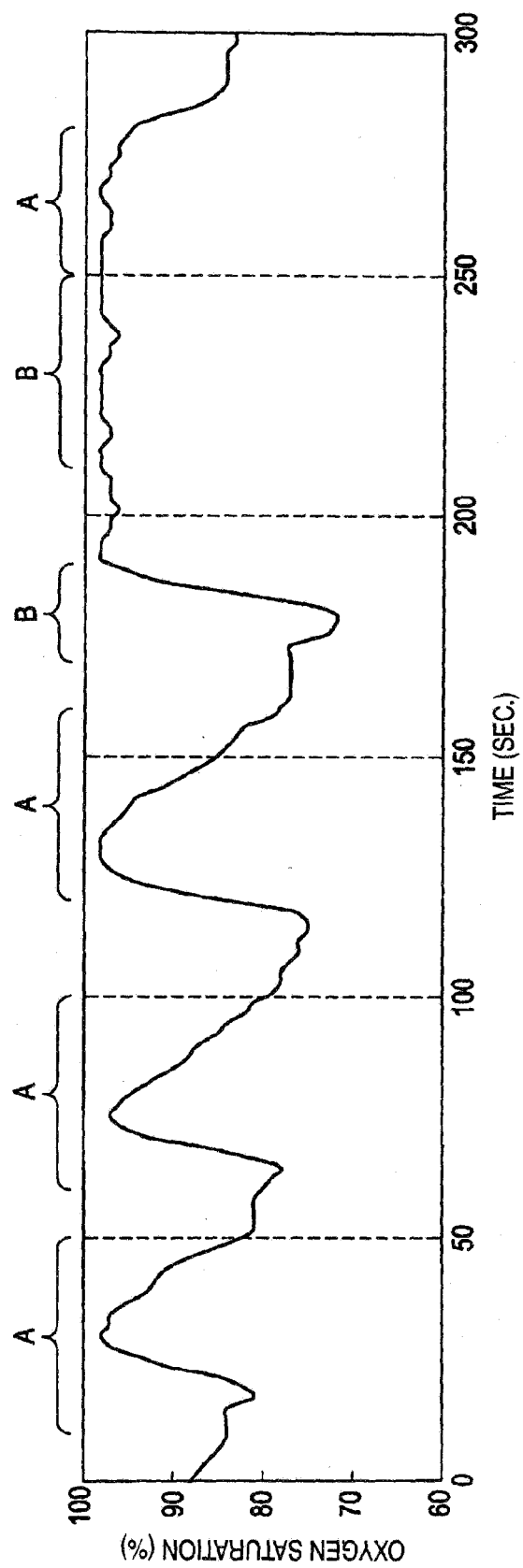
FIG. 6 is a view showing a temporal change of the blood oxygen saturation in the artery in a time zone corresponding to the temporal change of the blood oxygen saturation in the vein shown in FIG. 3.

FIG. 6 shows a temporal change of the blood oxygen saturation in the artery in a time zone corresponding to the temporal change of the blood oxygen saturation in the vein shown in FIG. 3. As shown in FIG. 6, in time zones (time zones which are indicated by "B" in the upper portion of the graph of FIG. 6) where the subject is suspected of being in a central apnea condition during sleep, the blood oxygen saturation in the artery is once increased by the respiration immediately before entering the central apnea condition, and thereafter the temporal change is very small.

Therefore, the blood oxygen saturation measuring apparatus 200 monitors the blood oxygen saturation in the artery in addition to the monitoring of the amplitudes of the frequency components corresponding to the respiratory rate of the subject, and therefore can more correctly determine that the subject is in a central apnea condition.

Figure 7:
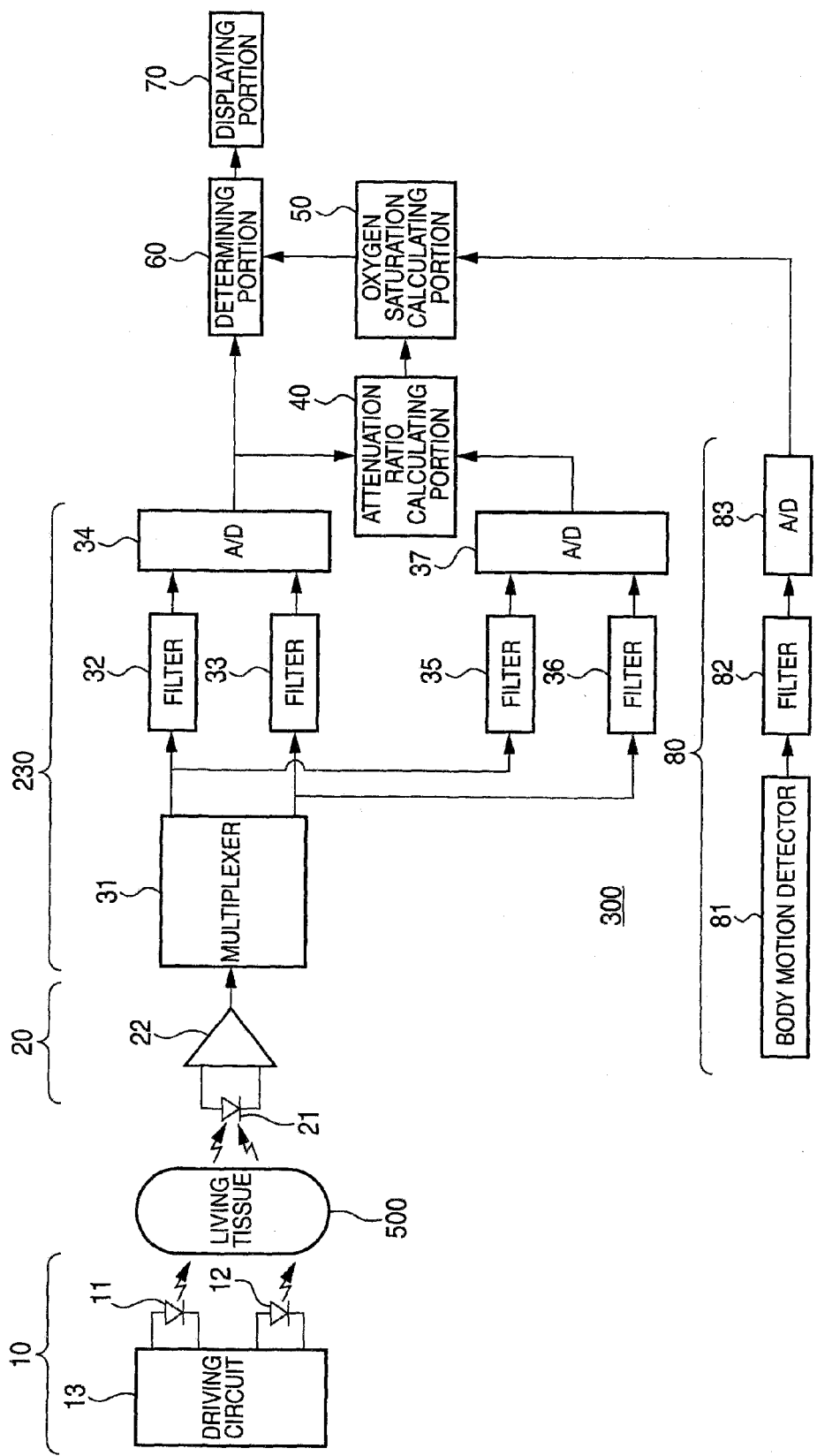
FIG. 7 is a functional block diagram of a blood oxygen saturation measuring apparatus of a further example of the embodiment of the invention.

FIG. 7 is a functional block diagram of a blood oxygen saturation measuring apparatus 300 of a further example of the embodiment of the invention. In the example, the configurations which are identical with those of the blood oxygen saturation measuring apparatus 100 which has been described with reference to FIG. 1 or the blood oxygen saturation measuring apparatus 200 which has been described with reference to FIG. 5 are denoted by the same reference numerals, and their description is omitted.

As shown in FIG. 7, the blood oxygen saturation measuring apparatus 300 includes a body motion detecting portion 80 in addition to the configuration of the blood oxygen saturation measuring apparatus 200. The body motion detecting portion 80 has a body motion detector 81, a filter 82, and an A/D converter 83.

The body motion detector 81 detects a change (body motion) of the body position of the subject. Specifically, the body motion detector 81 includes an acceleration sensor and gyro sensor which are to be fixed to, for example, the surface of the body of the subject, and intermittently or continuously supplies an electric signal of a level which corresponds to the current body position of the subject, to the filter 82. When the subject changes the body position, the body motion detector 81 outputs the electric signal in which the level is gradually changed from the value corresponding to the body position before the change to that corresponding to the body position after the change, in accordance with the change of the body position.

The filter 82 extracts a variation component of the electric signal from the body motion detector 81 based on a change of body motion of the subject, outputs the variation component to the A/D converter 83, and filters out components other than the variation component. The A/D converter 83 digitizes the electric signal which is supplied from the filter 82, and outputs the digital signal to the oxygen saturation calculating portion 50. Therefore, the oxygen saturation calculating portion 50 receives the electric signal the level of which reflects the change of body motion of the subject, from the body motion detecting portion 80. In the example, the electric signal output from the body motion detecting portion 80 is a signal which has a constant level in a state where the subject rests in a constant position, and in which, in the case where the subject changes the body position, the level is varied in substantially proportion to the displacement distance of the body motion per unit time.

The oxygen saturation calculating portion 50 corrects the blood oxygen saturation in the vein which is calculated on the basis of the attenuation ratio $R_{(R/IR)}$, based on the electric signal from the body motion detecting portion 80. Specifically, for example, the oxygen saturation calculating portion 50 removes a temporal variation component which is produced in the calculated blood oxygen saturation in the vein, during a period when the level of the electric signal from the body motion detecting portion 80 is temporally varied.

FIG.S. 8 and 9 show, in an upper stage, examples of signal waveforms which are input into the filters 32, 33, respectively, and the waveform of the blood oxygen saturation in the vein which is calculated in the oxygen saturation calculating portion 50 on the basis of the signal waveforms, and, in a lower stage, an example of the level variation of an electric signal due to body motion of the subject. The waveform of the blood oxygen saturation in the vein which is shown in the upper stage of FIG. 8 is a waveform in the case where the oxygen saturation calculating portion 50 does not perform the correction due to the electric signal from the body motion detecting portion 80, and that of the blood oxygen saturation in the vein which is shown in the upper stage of FIG. 9 is a waveform in the case where the oxygen saturation calculating portion 50 performs the correction.

Figure 8:
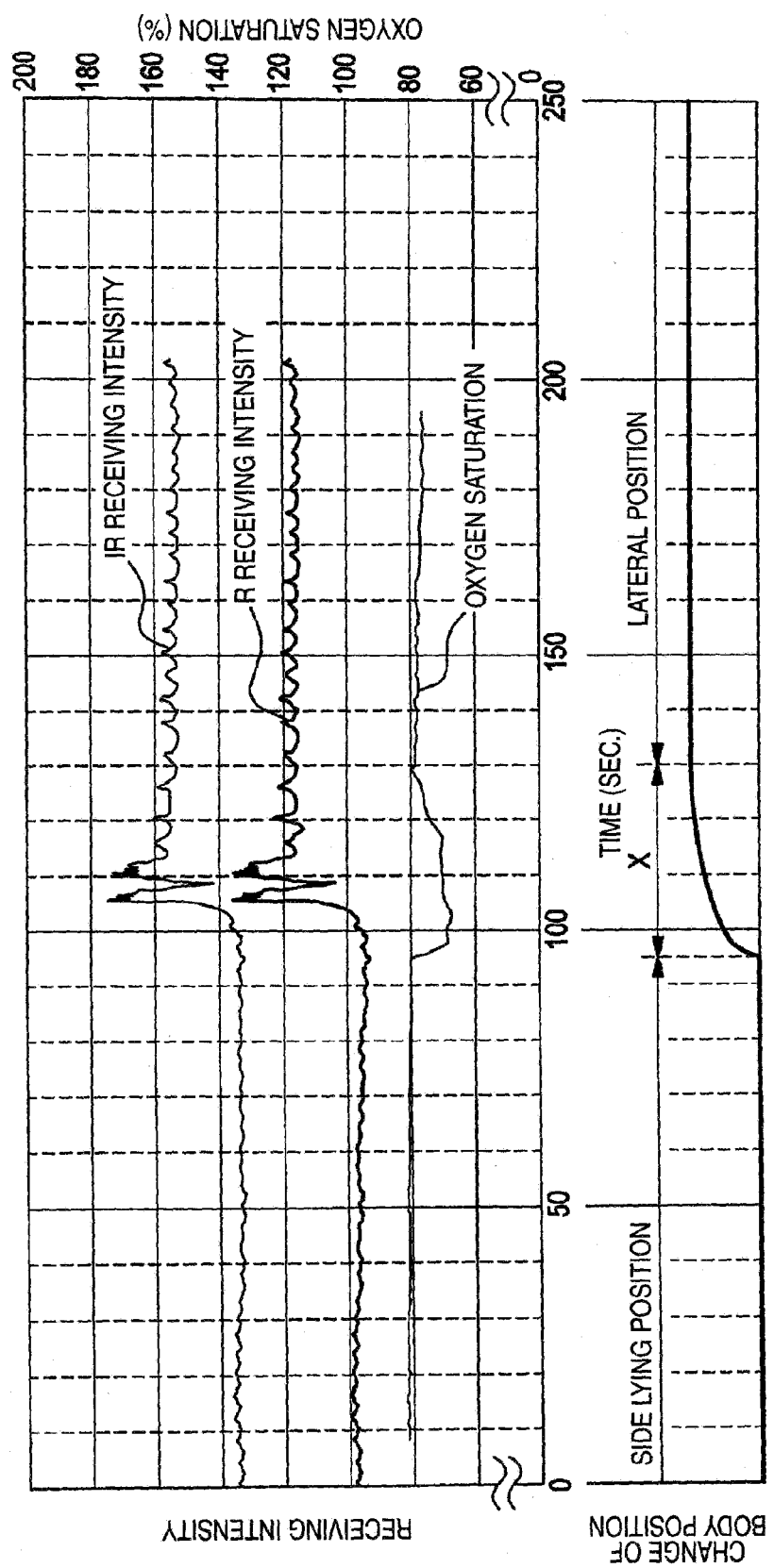
FIG. 8 is a view showing, in an upper stage, examples of signal waveforms which are input into the filters, respectively, and the waveform of the blood oxygen saturation in the vein which is calculated in an oxygen saturation calculating portion on the basis of the signal waveforms, and, in a lower stage, an example of the level variation of an electric signal due to body motion of the subject.
Figure 9:
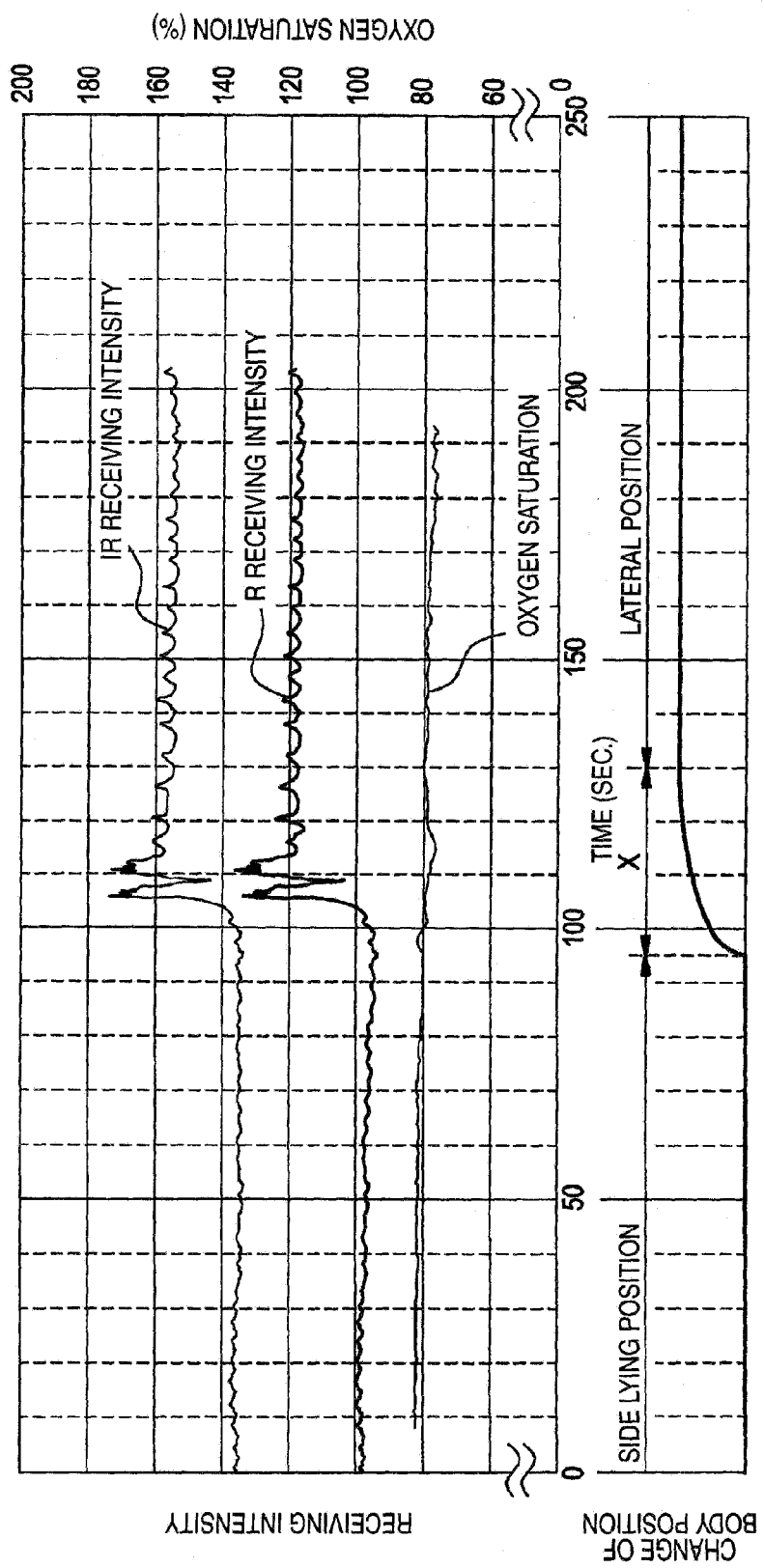
FIG. 9 is a view showing, in an upper stage, examples of signal waveforms which are input into the filters, respectively, and the waveform of the blood oxygen saturation in the vein which is calculated in the oxygen saturation calculating portion on the basis of the signal waveforms, and, in a lower stage, an example of the level variation of an electric signal due to body motion of the subject.

As shown in FIG. 8, in the case where the subject rests in a body position of the side lying position or the lateral position, the electric signal based on body motion of the subject has a constant value. By contrast, when the body position is changed from the lateral position to the side lying position, the level of the electric signal is varied in accordance with the change of the body position. Then, the oxygen saturation calculating portion 50 removes a temporal variation component which is produced in the blood oxygen saturation in the vein, during a period when the variation occurs (the time zones indicated by "X" in the lower stages of FIG.S. 8 and 9), whereby, in the temporal change produced in the blood oxygen saturation in the vein, a change due to the influence of body motion of the subject is corrected (FIG. 9). Although not shown in FIG.S. 8 and 9, in the case where the blood oxygen saturation in the artery is to be calculated, the oxygen saturation calculating portion 50 may correct the blood oxygen saturation in the artery in a similar manner as the blood oxygen saturation in the vein.

As described above, the blood oxygen saturation measuring apparatus 300 of the example can correct the influence of body motion of the subject in the temporal change of the blood oxygen saturation in the vein which is calculated by the oxygen saturation calculating portion 50. Therefore, the temporal variation of the blood oxygen saturation in the vein can be made more close to the change due to the respiration of the subject.

The blood oxygen saturation measuring apparatuses 100, 200, 300 which have been described above can detect at an earlier timing an obstructive apnea condition which leads to pulmonary hypertension and also right-sided heart failure due thereto. Moreover, the apparatuses can detect not only an obstructive apnea condition but also a central apnea condition, and hence can detect more correctly a symptom of respiration failure of the subject.

In the embodiment, unlike a respiration detecting system based on impedance detection, such as an electrocardiogram, respiration is not detected from a dynamic impedance change due to thoracic motion, but respiration is measured from a quantized blood oxygen saturation. Therefore, the respiratory management can be performed more stably. As compared with a respiration detecting system based on impedance detection, it is not required to attach a plurality of electrodes, and hence the burden on the subject is small.

Although the invention has been described with the embodiments, the technical scope of the invention is not restricted to the scope of the description of the embodiment. It is obvious to those skilled in the art that various changes or improvements can be made on the embodiment.

According to an aspect of the invention, it is possible to detect at an earlier timing that the subject enters an obstructive apnea condition. Furthermore, the variation component of the blood volume of the vein is extracted, and the amplitude is monitored. Therefore, it is possible to detect a central apnea condition during sleep which is hardly detected based on only the blood oxygen saturation that is calculated by using the pulse wave component of the artery. Simply when the light emitter and the light receiver are placed on the tip of a finger, an ear lobe, or the like of the subject, moreover, the measurement is enabled. Therefore, the burden on the subject can be reduced and the measurement is insusceptible to body motion and the like.

What is claimed is:

1. A blood oxygen saturation measuring apparatus comprising:
 a light emitter adapted to emit, to living tissue of a subject, at least two light beams which have different wavelengths from each other;
 a light receiver adapted to receive the light beams which are transmitted through or reflected from the living tissue, the light receiver which converts the received light beams to electric signals corresponding to receiving intensities of the light beams, respectively;
 an extractor which extracts frequency components corresponding to changes of the receiving intensities according to a variation of a blood volume of a vein in the living tissue due to respiration of the subject, from the electric signals, respectively;
 an attenuation ratio calculator which calculates a first attenuation ratio based on amplitudes of the extracted frequency components;
 an oxygen saturation calculator which calculates a first blood oxygen saturation in the vein based on the first attenuation ratio; and
 a determiner which determines that the subject is in an obstructive apnea condition, when the first blood oxygen saturation in the vein shows a decreasing trend for a predetermined time period or longer, wherein
 the extractor extracts pulsation components corresponding to changes of the receiving intensities according to pulsation of an artery in the living tissue, from the electric signals, respectively,
 the attenuation ratio calculator calculates a second attenuation ratio based on amplitudes of the pulsation components,
 the oxygen saturation calculator calculates a second blood oxygen saturation in the artery based on the second attenuation ratio, and
 the determiner determines that the subject is in a central apnea condition, when the amplitudes of the frequency components are smaller than a predetermined value for a predetermined time period or longer and the second blood oxygen saturation in the artery does not show a decreasing trend.

2. The blood oxygen saturation measuring apparatus according to claim 1, further comprising:
 a body motion detector which detects a change of body motion of the subject,
 wherein the oxygen saturation calculator corrects the calculated first blood oxygen saturation based on the change of the body motion.

* * * * *